United States Patent [19]

Carlson et al.

[11] 4,018,218
[45] Apr. 19, 1977

[54] METHOD AND APPARATUS FOR SLEEP INDUCTION

[76] Inventors: James E. Carlson, 9233 Carthay Circle, Spring Valley, Calif. 92077; Robert E. Urmston, 4405 Niagara Ave., San Diego, Calif. 92107

[22] Filed: Mar. 12, 1975

[21] Appl. No.: 557,593

[52] U.S. Cl. .......................... 128/1 C; 128/420 A; 128/422
[51] Int. Cl.[2] ........................................ A61N 1/34
[58] Field of Search ............ 128/1 C, 2.1 R, 419 R, 128/420, 421, 422, 423, 410

[56] References Cited

UNITED STATES PATENTS

| | | | |
|---|---|---|---|
| 3,122,137 | 2/1964 | Erlanger | 128/410 |
| 3,160,735 | 12/1964 | Aufricht | 128/410 |
| 3,320,947 | 5/1967 | Knoll | 128/1 C |
| 3,376,870 | 4/1968 | Yamamoto et al. | 128/1 C |
| 3,540,453 | 11/1970 | Sugimori | 128/422 |
| 3,699,970 | 10/1972 | Brindley et al. | 128/419 R |
| 3,762,396 | 10/1973 | Ballentine et al. | 128/1 C |
| 3,835,833 | 9/1974 | Limoge | 128/1 C |

FOREIGN PATENTS OR APPLICATIONS 1,220,031 1/1960 France ........................ 128/1 C

OTHER PUBLICATIONS

Smith et al., "American Journal of Medical Electronics," Jan.–Mar. 1965, pp. 38–41.

*Primary Examiner*—William E. Kamm
*Attorney, Agent, or Firm*—Brown & Martin

[57] ABSTRACT

An apparatus and method to induce sleep in a patient that utilizes an oscillator to control the frequency of electric impulses received by the patient. First and second multivibrators generate the signals necessary to stimulate the central nervous system by conduction through the optic nerve tract, and also to generate a visual aura caused by stimulation of the retina of the eye. An amplifier amplifies the signals generated by the multivibrators and electrodes transmit the amplified signal to the patient. The various components of the apparatus may be stored in an eye frame structure wherein eye lid electrode pads are held in place contiguous the eyes of the patient, and wherein mastoid electrode pads are held in place by means of the frame ear hooks.

23 Claims, 6 Drawing Figures

METHOD AND APPARATUS FOR SLEEP INDUCTION

BACKGROUND OF THE INVENTION

The present invention relates to apparatus for artificially inducing sleep in a patient.

In recent years, insomnia has become the subject of medical and psychological treatment and study with the direction being to devise a system which will conveniently and efficiently induce sleep. Electric impulse devices have gained in favor since chemotherapy treatments often involve substances that act upon the central nervous system and there is a growing aversion to the utilization of chemicals to cure what may otherwise be treated.

Electrosleep is elicited by a train of electrical pulses in the form of a waveshape such as sinusoidal, square, triangular and spike. The spike form is presently gaining favor and is generally of 1 to 2 milliseconds duration at about 20 volts amplitude and 100 microamperes current. Other waveshapes have the disadvantage of causing pain at the electrodes for the equivalent amplitude of the spike. The repetition frequency employed for all waveshapes is generally between 5 and 200 cycles depending somewhat on the subjective choice of the patient. The amplitude of the waveshape is also subjective to the desire or fancy of the patient and for this purpose it is desirable for the equipment to be conveniently adjustable. During treatment, the patient feels nothing and is unaware of the electrical stimulation. For waveshapes other than the spike, with pulse durations of greater than 2 milliseconds the patient may be aware of a visual sensation caused by the electrical stimulation of the retina of the eye, and this stimulation appears to effect the ganglia in the retina of the eye. Use of different waveshapes have been the result of investigation for the optimized waveshape and the instant invention presents what thus far is believed to be a highly effective waveform.

Electrodes have been standardized to placement, polarity and use of some contact enhancing substance. Placement of the electrodes is generally one electrode over each eye lid and one electrode over each mastoid. The polarity of the electrodes in the front or eye lid electrodes is negative and the back or mastoidal electrodes positive. The contact enhancing substances in use are conductive jellies developed for use in electroencephalography and electrocardiography, as well as physiological saline solution.

Electrosleep has proven to be a useful technique to elicit relaxation or sleep in a large number of people. The disadvantages of previous techniques are the time consumed by the treatment and temporary visual disturbances following the treatment. Time problems have limited its use clinically where clinicians must set up the apparatus, adjust it to the individual patient, monitor the treatment, and provide for bedspace for the treatment. The distortion of vision following the treatment is caused by the eye lid electrodes exerting pressure on the eyeball causing blurred vision for up to 30 minutes after the treatment. The instant invention is designed to overcome most of the handicaps of the prior art apparatus. Specifically it is directed toward rendering a useful apparatus portable and easy to apply, and also it is designed so that the least possible visual disturbances are afflicted on the patient by reducing the amount of time necessary to employ the treatment.

Among the prior art is the Hoody et al U.S. Pat. No. 3,160,159, Dec. 8, 1964. This patent describes the use of a multivibrator which produces a spike waveform that is designed to generate reticular formation stimulus signals. This patent also generally refers to the desirability to render an acceptable unit portable for use on the patient in the home or other areas outside of the hospital.

The prior art is deficient in providing a portable device which will both generate reticular formation stimulus signals as well as visual stimulus signals. A small, compact and conveniently worn device, that may be employed outside of the hospital or the physicians office has been required by the practitioners for some time.

SUMMARY OF THE INVENTION

It is a primary object of the instant invention to provide a novel and improved sleep induction device and method for generating sleep inducing signals in an efficient and safe manner.

Another object of the instant invention is the provision of a sleep induction device which generates visual stimulus signals as well as reticular formation stimulus signals.

Still another object of the instant invention is the provision of a sleep induction device that is portable and conveniently worn and can be utilized outside of the hospital or physicians office.

In accordance with the above designs, the present invention comprises apparatus that generates a waveform characterized by a spike wave having an amplitude that is dependent upon the subjective desires of the patient and a duration of less than 2 milliseconds to stimulate the reticular formation. A second pulse in the form of a square wave that has a duration of less than 100 milliseconds and an amplitude significantly less than 22 volts to stimulate a visual aura to physiologically induce relaxation or sleep.

The apparatus which generates the above mentioned waveform, comprises an oscillator means to generate the basic control frequency of 5 to 100 cycles per second, which oscillator controls a multivibrator that generates the visual stimulus, and a one-shot multivibrator which generates the reticular formation stimulus. An amplifier combines the two pulses and amplifies them and an attenuator controls that amplitude according to the subjective needs of the patient. Electrodes interface the device with the patient contiguous his eyes or frontal processes and mastoids. A timer is preset for the treatment duration at the end of which the power supply is cut off thereby shutting off electrical signals to the patient.

The various electrical components of the instant invention may be packaged within a template of an eyeframe, the eye lid electrodes being held by the lens frames, and the mastoid electrodes being disposed adjacent the mastoids by means of the template ear hooks. The templates may be of a slightly thicker than normal configuration and hollowed so as to house the electrical components hereinbefore described. Alternatively the electronic components of this system may be packaged separate from the electrodes which are conveniently disposed on a thin flexible band. A pair of cables may be utilized to deliver the signal from the electrical components to the electrodes.

The above and other aspects of the instant invention will be apparent as the description continues and when read in conjunction with the appended drawings.

DETAILED DESCRIPTION OF THE DRAWINGS

Figure 1:
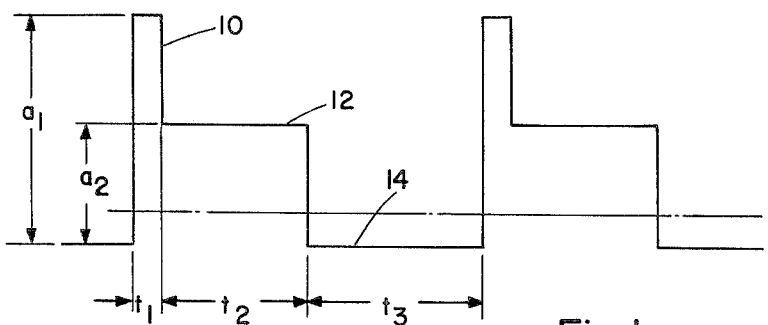
FIG. 1 is a diagram of the repetitive waveform that produces psychological and physiological sleep induction.

FIG. 1 illustrates the basic waveform utilized by the instant invention which both physiologically and psychologically act upon the central nervous system of the patient to produce relaxation or sleep. A spike signal 10 is responsible for the physiological induction of sleep and has a duration $t_1$ of less than 2 milliseconds and amplitude $a_1$ of less than 22 volts. The square wave 12 is a pulse with duration $t_2$ of less than 100 milliseconds and an amplitude $a_2$ significantly less than 22 volts and functions to stimulate a visual aura to psychologically induce sleep. It has been found effective to maintain the duration of the spike pulse 10 as a fixed interval. The duration $t_2$ of the square wave 12 is varied as a ratio of the sum of the durations $t_1$, $t_2$ of waves 10 and 12 divided by the time period $t_3$ permitted to allow the central nervous system to partially recover from the ionizing potential of pulses 10 and 12. This time period $t_3$ is selected to be longer than the neuron refractory period of the optic nerve tract. A small direct current, negative bias illustrated by waveform 14 and set by battery 105 (see FIG. 3), is employed during this recovery period to enhance the discharge rate of stored energy due to the small capacitive nature of the electrodes. The amplitudes $a_1$, $a_2$ of the pulses 10 and 12 and the time intervals between successive time pulses are adjusted to the subjective needs of the patient. During the pulse 10, the amplitude thereof is sufficiently high, usually 15 to 18 volts, to stimulate the central nervous system by conduction through the optic nerve tract to reduce conscious activity of the higher brain centers. During the pulse 12, the amplitude $a_2$ is a fixed ratio of the amplitude $a_1$ of pulse 10 divided by the amplitude $a_2$ of pulse 12 and amplitude $a_1$ is on the order of 7.5 to 9 volts and is of sufficient time duration $t_2$, greater than 5 milliseconds, to generate a visual aura caused by stimulation of the retina of the eye. The duration $t_1$ of pulse 10 is the physiological stimuli in that it is present without the patient being aware of it. The duration $t_2$ of pulse 12 is the psychological stimuli as it causes a pulsating visual effect and is of insufficient amplitude to be effective for reticular formation synchronization. Thus, the waveform produces a dual effect of stimulating the brain centers responsible for awareness and stimulating a visual aura.

Figure 2:
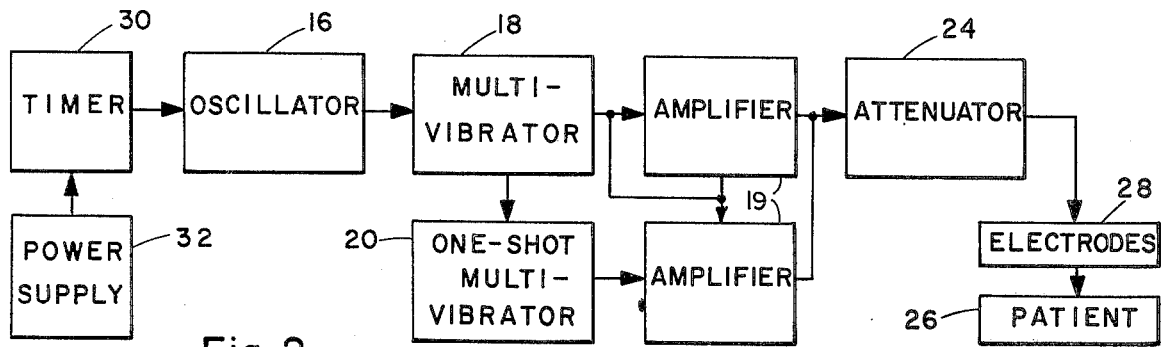
FIG. 2 is a block diagram of the electrical components that generate the waveform of FIG. 1.

Referring to FIG. 2, the apparatus which generates the waveform of FIG. 1 is characterized by an oscillator 16 which generates the basic control frequency of 5 to 100 cycles per second. The oscillator controls a multivibrator 18 which generates the visual stimuli denoted by the pulse 12 of FIG. 1. A one-shot multivibrator 20 generates the reticular formation stimulus or pulse 10 of FIG. 1. Amplifier means 19 combines the pulses 10 and 12 and amplifies them. The resulting signal is passed to the attenuator 24 that allows amplitude control of the pulses 10 and 12 to be adjusted to the subjective needs of the patient 26. The electrodes 28 interface the patient 26 with the entire system and a timer 30 is preselected for a particular treatment duration. At the end of the time interval the timer 30 shuts off the power supply 32 from the circuit. The power supply 32 may be selected for patient safety in case of a malfunction of the circuitry.

Figure 3:
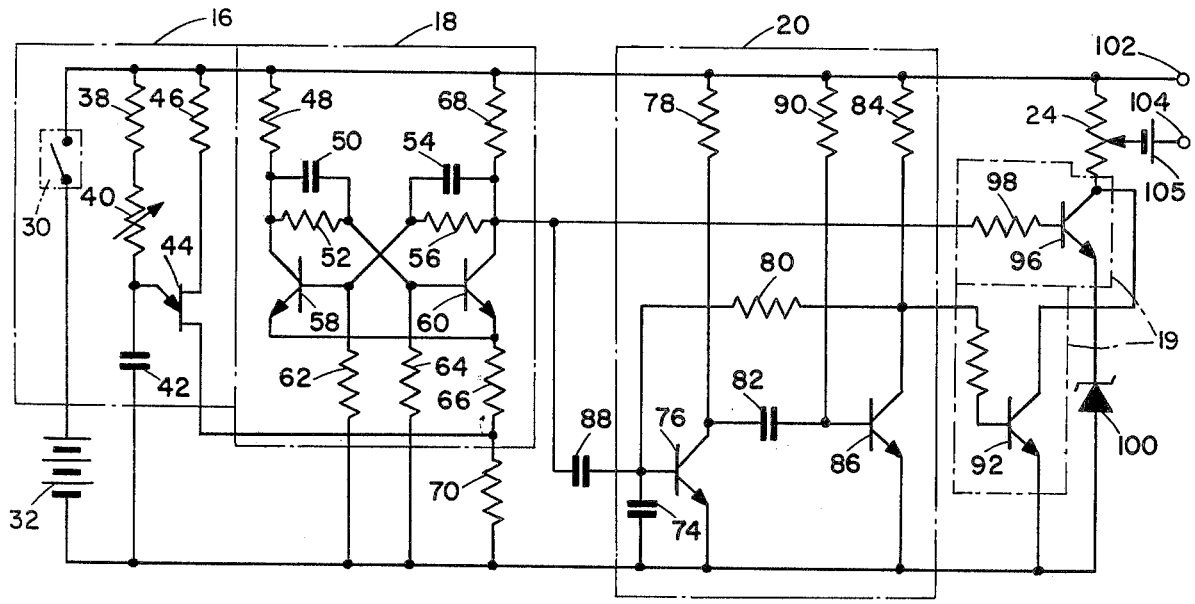
FIG. 3 is a circuit diagram of the electrical elements that comprise the components of FIG. 2.

FIG. 3 schematically illustrates the electronic circuitry necessary to produce the waveform of FIG. 1. The battery or rectified AC serving as the power supply 32 is selected to produce the maximum pulse amplitude of the spike pulse 10 that is permissible. This is for the safety of the patient to protect him from voltages approaching the electroconvulsive shock level. For this purpose the battery 32 may have a 22.5 volt capacity. The timer switch 30, as illustrated in FIG. 3, is closed by any suitable timer that may, for example, be timing selected for a 2 hour timing period. The basic timing period is by any suitable timer switch. Components 38, 40, 42, 44 and 46, which form a unijunction transistor relaxation oscillator comprise oscillator 16 of FIG. 2 and provides the signals to the multivibrator 18 which is denoted by the components 48, 50, 52, 54, 56, 58, 60, 62, 64, 66 and 68 through the emitter drive resistor 70 and is responsible for generating the pulse 12 of FIG. 1 through line 97 to resistor 98 and transistor 96 of amplifier 19. The one-shot multivibrator 20 is denoted by the components 74, 76, 78, 80, 82, 84, 86 and 90, and serves to sense the positive going condition of transistor 60 through capacitor 88 giving a single positive pulse 10 on the collector of amplifying transistor 92. The interval of pulse 10 is determined by the time constant of capacitor 82 and resistor 90 and the transistor 92 is the pulse amplifier 19 for the pulse 10 and when conducting there is a full supply of voltage across the potentiometer or attenuator 24. This voltage is between the negative level set by power source or battery 105 and the pulse output of amplifier 19. The negative bias for recovery is from battery 105. Transistor 96 also senses a positive going condition of transistor 60 through resistor 98 and conducts as long as transistor 60 is out of conduction. This corresponds to the time period $t_2$ for pulse 12 of FIG. 1. Transistor 96 is biased to less than power supply voltage by the zener diode 100 and this voltage is produced across potentiometer 94 as long as transistor 60 is out of conduction. This corresponds to amplitude $a_2$ of pulse 12 of FIG. 1. Electrodes that are connected to the patient are connected to terminals 102 and 104 of potentiometer 94 in such a way as to make the front or eye lid electrodes negative and the back or mastoidal electrodes positive. Terminal 104 is utilized for the eye lid electrodes and terminal 102 is utilized for the mastoidal electrodes. The upper and lower voltage levels to the patient is adjusted by the potentiometer or attenuator 24, and the frequency is adjusted by the rheostat 40 so as to optimize the effect on the patient.

Figure 4:
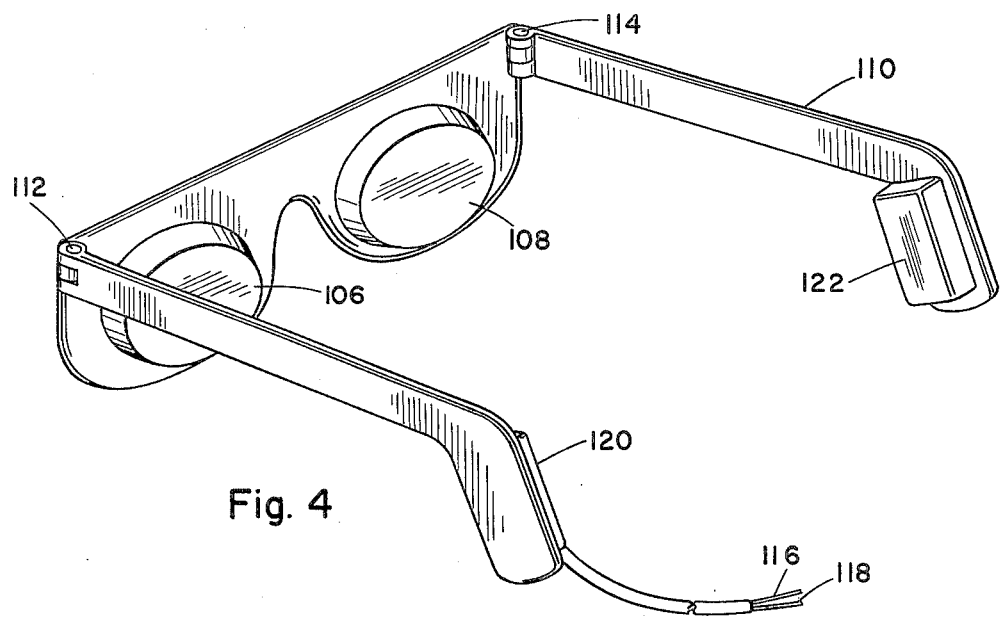
FIG. 4 illustrates one embodiment of an electrode holder to be worn on a patient's head.

In FIG. 4, the eye lid electrodes 106, 108 are shown assembled to a rigid frame 110 which resembles an ordinary eye glass frame being hinged at points 112 and 114 for easy storage. The cables 116, 118 connect the eye lid electrodes 106, 108 and the mastoidal electrodes 120, 122 to the terminals 102, 104. The mastoidal electrodes 120, 122 are disposed on the inner surface of the ear hooks of the templates of the frame 110. Alternatively, electrodes may be connected to the frontal processes instead of the eye lids.

Figure 5:
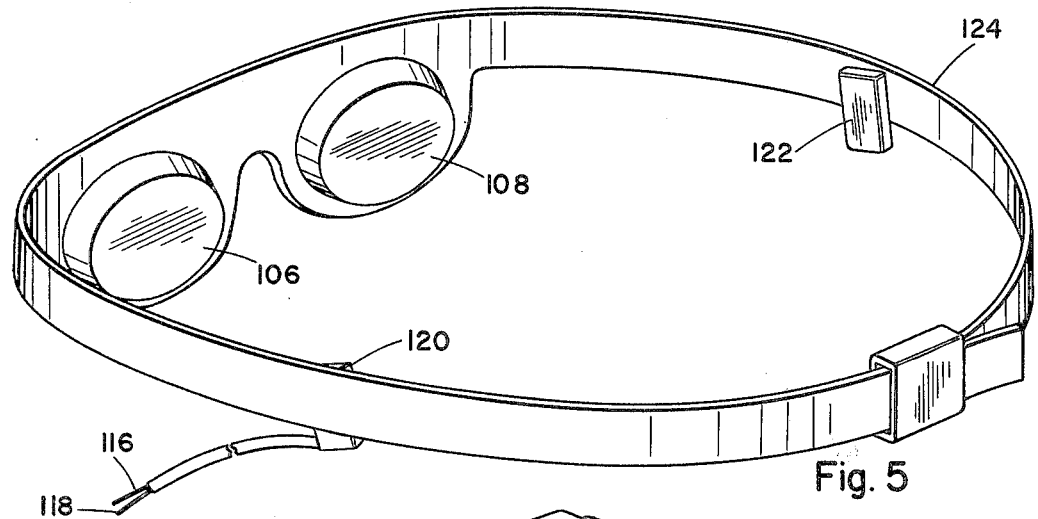
FIG. 5 is a perspective view of a band type electrode holder.
Figure 6:
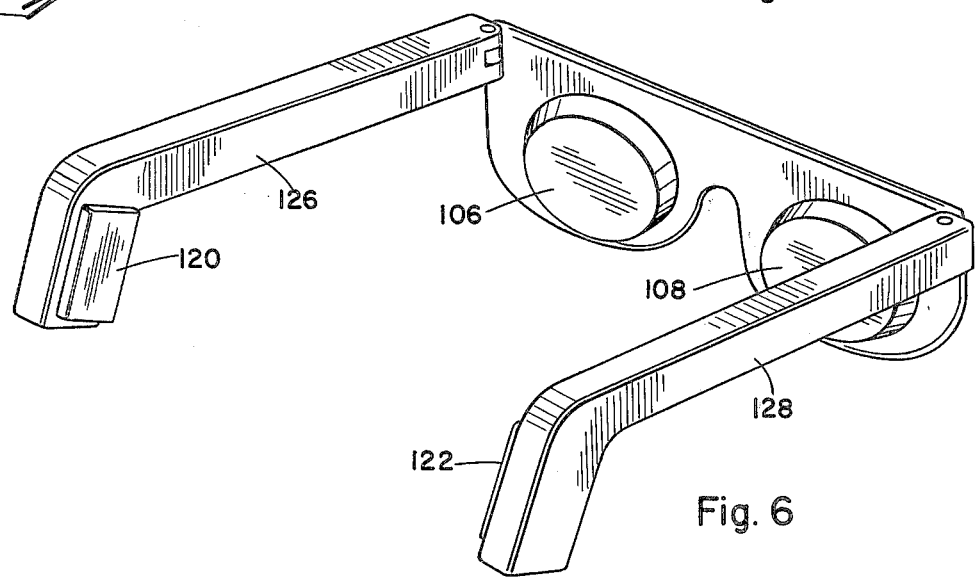
FIG. 6 illustrates an alternate embodiment electrode holder which is designed to portably package the electrical components therewithin.

FIGS. 5 and 6 illustrate modifications of the electrode holder. FIG. 5 illustrates a flexible band 124 to which the eye lid electrodes 106, 108 and the mastoidal electrodes 120, 122 are appropriately placed. FIG. 6 illustrates a holder quite similar to the holder 110 except that the templates 126, 128 are of greater width and capable of housing the components hereinbefore described that generate the waveform of FIG. 1.

The eye lid electrodes 106, 108 of the various embodiments are constructed so as to fit the contour of the eyeball. The electrode pads are made of a material that allows good contact with the eye lids and are slightly dampened with saline solution.

The invention hereinbefore described is quite conveniently utilized by the patient and efficient and safe for its intended use of inducing relaxation or sleep in a patient. It functions to reduce physiological and psychological stress so as to permit the patient to obtain relaxation or sleep as desired.

The device has been shown to have an anesthetic supplemental effect, by reducing the amount of anesthetic required during surgery.

Modifications or adaptations in the method and materials of the fabrication, on the configuration or assemblage of the constituent components are readily permissible within the scope of the instant invention which changes are intended to be embraced therewithin.

Having described our invention, we now claim:

1. An apparatus to induce sleep in a patient which comprises:
    means for generating electrical cycle pulses having a basic control frequency,
    first means responsive to said electrical pulses for generating reticular formation stimulus signals that are first in the cycle,
    second means for generating visual stimulus signals that are second in the cycle,
    third means for generating recovery signals that are third in the cycle,
    and electrode means for transmitting the cycle of signals to the patient.

2. The apparatus of claim 1, including amplifier means for amplifying the signals generated by the first and second means.

3. The apparatus of claim 2, wherein the signal generated by the second means is a square wave.

4. The apparatus of claim 3, wherein the square wave has an amplitude $a_2$ of less than 10 volts and a duration of less than 100 milliseconds.

5. The apparatus of claim 1, wherein the first and second means are multivibrators.

6. The apparatus of claim 1, including attenuating means for attenuating the signals transmitted to the patient.

7. The apparatus of claim 1, wherein the signal generated by the first means is a spike wave of amplitude $a_1$ less than 22 volts, and a duration of less than 2 milliseconds, the signal generated by the second means is a square wave of amplitude $a_2$ less than 10 volts and a duration of less than 100 milliseconds, and
    wherein the amplitudes $a_1$ and $a_2$ are maintained in a fixed ratio of $a_1/a_2$.

8. The apparatus of claim 1, wherein the recovery signals are a square wave of negative amplitude.

9. The apparatus of claim 1, including means for packaging the oscillator means, and first and second means for support on a patient's head,
    and the electrode means disposed on said packaging means for contact in the vicinity of the eyes and mastoids.

10. The apparatus of claim 9, wherein said packaging means comprises a pair of templates,
    and the electrode means comprises mastoid electrodes connected to the templates for connection to the patient's mastoids.

11. The apparatus of claim 9, wherein said packaging means comprises an eye frame,
    and the electrodes comprise a pair of eye lids electrodes disposed on said eye frame contiguous the eye lids.

12. The apparatus of claim 1, wherein:
    the first in cycle signal generated for each cycle is a spike wave.

13. The apparatus as claimed in claim 1 wherein:
    said first signal having a pulse width about 50 times that of the second signal and the second signal having about the same pulse width as the third signal.

14. The apparatus as claimed in claim 13 wherein:
    said first signal having a magnitude about twice that of the second signal and the third signal having a polarity opposite that of the first and second signals, and having a magnitude substantially smaller than the second signal.

15. A method of inducing sleep in a patient which comprises the steps of:
    applying reticular formation signals to a patient,
    then applying visual stimulus signals to a patient,
    and then applying negative recovery signals to the patient.

16. The method as claimed in claim 15 including the steps of:
    generating the reticular formation signal, visual stimulus signal and recovery signal, consecutively and electrically connected together,
    and cycling said signals.

17. The method of claim 16, including the step of, amplifying the reticular formation and visual stimulus signals prior to applying them to the patient.

18. The method of claim 16, including the step of, cycling the reticular formation and visual stimulus signals and recovery signals for repetitive application to the patient.

19. The method of claim 16 including the step of, attenuating the signals applied to the patient.

20. The method as claimed in claim 16 including the steps of:
    generating the reticular formation signals so that each signal has a pulse width about 50 times that of the pulse width of the visual stimulus signals,
    and generating the recovery signal so it has a pulse width about the same as that of the visual stimulus signal.

21. The method as claimed in claim 16 including the steps of:

generating a reticular formation signal that has a magnitude about twice that of the visual stimulus signal, and generating a negative recovery signal that has a polarity opposite that of the reticular formation signal and visual stimulus signal and is substantially less in magnitude than said visual stimulus signal.

22. The method as claimed in claim 20 being characterized by:
the pulse width of said reticular signal is less than 2 milliseconds and the pulse width of said visual stimulus signal is less than 100 milliseconds.

23. The method as claimed in claim 20 including the steps of:
generating a reticular formation signal that has a magnitude of less than 22 volts, and generating a visual stimulus signal that has a magnitude of less than 9 volts.

* * * * *